(12) United States Patent
Windecker et al.

(10) Patent No.: US 7,351,311 B2
(45) Date of Patent: Apr. 1, 2008

(54) METHOD FOR PURIFYING TETRAHYDROFURAN BY DISTILLATION

(75) Inventors: Gunther Windecker, Ludwigshafen (DE); Alexander Weck, Freinsheim (DE); Rolf-Hartmuth Fischer, Heidelberg (DE); Markus Rösch, Oppenheim (DE); Nils Bottke, Mannheim (DE); Michael Hesse, Worms (DE); Stephan Schlitter, Ludwigshafen (DE); Holger Borchert, Offstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 315 days.

(21) Appl. No.: 10/505,774

(22) PCT Filed: Feb. 28, 2003

(86) PCT No.: PCT/EP03/02045

§ 371 (c)(1),
(2), (4) Date: Aug. 26, 2004

(87) PCT Pub. No.: WO03/074507

PCT Pub. Date: Sep. 12, 2003

(65) Prior Publication Data

US 2005/0258025 A1    Nov. 24, 2005

(30) Foreign Application Priority Data

Mar. 2, 2002 (DE) ............................... 102 09 632

(51) Int. Cl.
*B01D 3/14* (2006.01)
*C07D 307/08* (2006.01)

(52) U.S. Cl. ..................... 203/75; 203/14; 203/78; 203/99; 203/DIG. 19; 549/429; 549/509

(58) Field of Classification Search ............ 203/74–80, 203/14, 99, DIG. 19; 549/429, 509
See application file for complete search history.

(56) References Cited

U.S. PATENT DOCUMENTS 4,332,645 A    6/1982    Mueller et al.
4,912,236 A    3/1990    Palm et al.

(Continued)

FOREIGN PATENT DOCUMENTS

DE    29 30 144    2/1981

(Continued)

OTHER PUBLICATIONS

Translation of JP 2639463.

(Continued)

*Primary Examiner*—Virginia Manoharan
(74) *Attorney, Agent, or Firm*—Novak Druce + Quigg LLP

(57) ABSTRACT

Crude water-containing tetrahydrofuran is purified by passing the crude tetrahydrofuran through three distillation columns, withdrawing water from the bottom of the first column, recycling water-containing tetrahydrofuran from the top of the second column into the first column, passing a sidestream of the first column into the second column, recycling the bottom product of the third column into the first column, and withdrawing a distillate at the top of the first column. Additionally, a sidestream of the second column is passed into the third column and the purified tetrahydrofuran is recovered as the top product of the third column.

1 Claim, 1 Drawing Sheet

U.S. PATENT DOCUMENTS 5,030,328 A * 7/1991 Fischer et al. ................ 203/80
6,780,289 B2 * 8/2004 Godbole ..................... 203/79
6,846,389 B2 * 1/2005 Kaibel et al. ................. 203/1

FOREIGN PATENT DOCUMENTS

DE  37 26 805  2/1989
DE  100 21703  11/2001

OTHER PUBLICATIONS

Translation of JP 2639464.
Translation of JP 2639463, Published: Aug. 13, 1997.
Translation of JP 2639464, Published: Aug. 13, 1997.

* cited by examiner

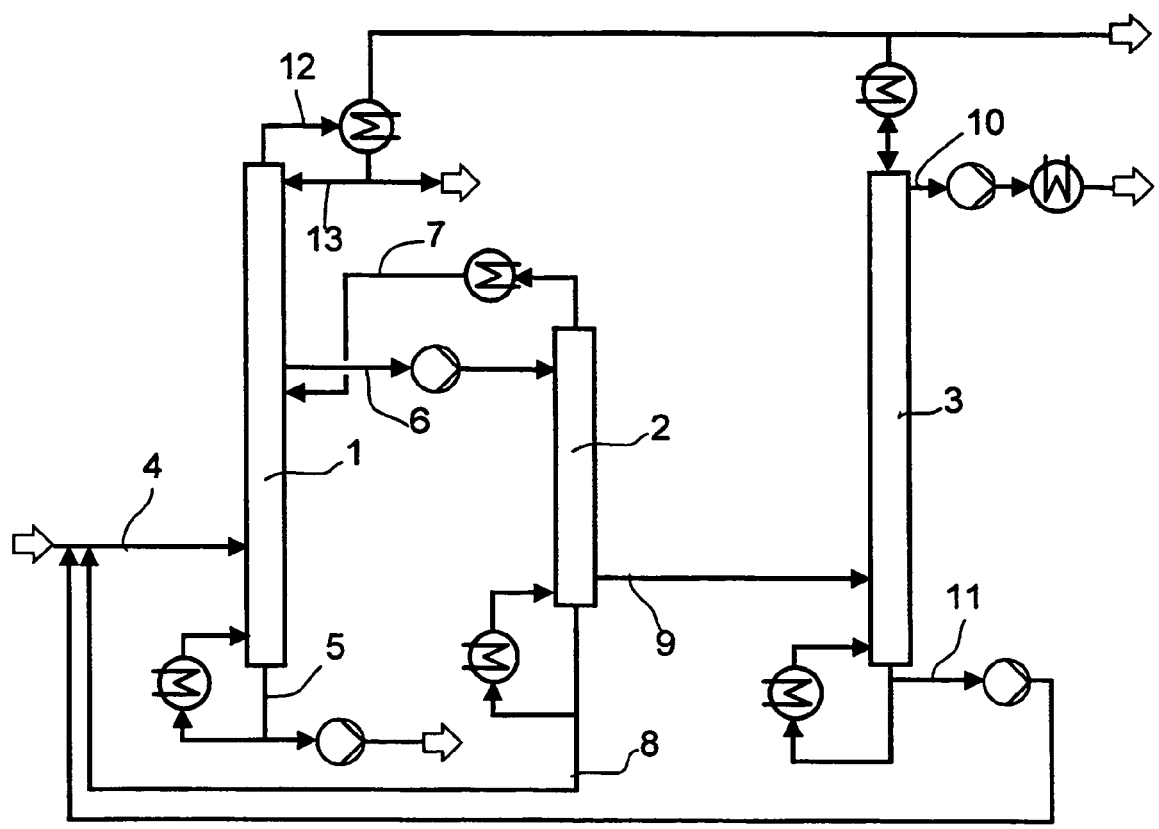

METHOD FOR PURIFYING TETRAHYDROFURAN BY DISTILLATION

The invention relates to a continuous process for distillative purification of tetrahydrofuran (THF).

The preparation of THF by dehydration of 1,4-butanediol over acid catalysts is described, for example, in DE-A 29 30 144 and leads to crude THF products having water contents of from 18 to 28% by weight and contents of up to 5% by weight of impurities (such as 2,3-dihydrofuran and 2- and 3-methyltetrahydrofuran) resulting from the synthesis.

The recovery of pure THF from such crude products is the purpose of a process disclosed by DE-A 37 26 805 for distillatively purifying crude water-containing THF by passing it through three distillation columns, which comprises passing a sidestream of the first column into the second, recycling the top product of the third column into the first column, withdrawing distillate at the top of the first column and recovering the pure tetrahydrofuran from the sidestream of the third column.

The preparation of THF by gas phase hydrogenation of maleic anhydride (MA) is a reaction which has been known for many years and is described, for example, in JP-B 2639463 and JP-B 2639464. The water-containing crude products obtained differ in particular from those obtained by butanediol dehydration by their higher fraction of components whose boiling points only differ slightly from the boiling point of THF, known as narrow-boiling components. The narrow-boiling components of THF include in particular methanol, ethanol and butyraldehyde, and also azeotropes thereof with THF and/or water.

The water-containing crude THF products from the gas phase hydrogenation of MA are not sufficiently purified by the process disclosed by DE-A 37 26 805 to fulfill the THF purity requirements relating in particular to the further processing of THF, for example to give PTHF.

It is an object of the invention to provide an improved process which economically facilitates the recovery of THF in high purity from water-containing crude THF products. It shall be possible to achieve these purities independently of the method of synthesis.

We have found that this object is achieved by a process for distillatively purifying crude water-containing tetrahydrofuran by passing the crude tetrahydrofuran through three distillation columns, withdrawing water from the bottom of the first column, recycling water-containing tetrahydrofuran from the top of the second column into the first column, passing a sidestream of the first column into the second column, recycling the bottom product of the third column into the first column, and withdrawing a distillate at the top of the first column, which comprises passing a sidestream of the second column into the third column and recovering the pure tetrahydrofuran as the top product of the third column.

The process according to the invention is applicable to crude, water-containing THF which was obtained by highly varying production processes. It is particularly suitable for crude THF products resulting from MA hydrogenation. It facilitates the recovery of highly pure THF and reliably removes the narrow-boiling components.

BRIEF DESCRIPTION OF THE DRAWING

The FIGURE shows an embodiment of the process utilizing three columns connected in series.

In the novel process, the distillative purification of crude water-containing THF which was preferably obtained by hydrogenation of MA is carried out in three columns connected in series as shown by the FIGURE. The columns are operated in a manner known per se, and the first column (1) is operated with a pressure of 1.3 bar with at least 10, preferably from 30 to 70, more preferably from 45 to 55, theoretical plates and a reflux ratio, based on the sidestream (5) of from 0.5 to 5, the second column (2) with at least 10, preferably from 30 to 70, more preferably from 45 to 55, theoretical plates, a pressure of from 5 to 10 bar, preferably from 7 to 9 bar, more preferably 8 bar, and the third column (3) with at least 10 theoretical plates, preferably from 30 to 70 plates, more preferably from 45 to 55 theoretical plates, at a pressure of from 0.9 to 2 bar, preferably from 1 to 1.5 bar and more preferably 1.3 bar and a reflux ratio of about 3.8.

Each of the three columns (1), (2) and (3) has at least one theoretical plate, which is characterized by the vapor stream formed and the liquid reflux of the plate being fed past each other in countercurrent. The internal fitments of the columns (1), (2) and (3) may comprise dumped packings, fabric packings or sheet metal packings, or trays such as valve trays, tunnel-cap trays or sieve trays. A definition of a theoretical plate may be found, for example, in E.-U. Schlunder, F. Thurner, Destillation, Absorption, Extraktion, Thieme Verlag 1986, page 66 and pages 131-132.

The crude water-containing THF which was obtained by gas phase hydrogenation of MA generally consists of 61% by weight of THF, 4% by weight of n-butanol (n-BuOH), 0.7% by weight of methanol (MeOH), 0.5% by weight of ethanol (EtOH), 1% by weight of propanol (ProOH), 400 ppm of gamma-butyrolactone (GBL), 120 ppm of butyraldehyde (BA), 100 ppm of butyl methyl ether (BME), further O-functionalized CH compounds in concentrations <200 ppm, and also water.

Introduction into the first column is effected at the side through the inlet (4). The inlet (4) is conveniently disposed in the lower half above the bottom of the column. According to the invention, it has been found that the feed should be disposed between the 1st and 30th theoretical plate, preferably between the 1st and 20th theoretical plate, most preferably between the 1st and 10th theoretical plate. Water and high-boiling components which have a higher boiling point than THF, such as gamma-butyrolactone, ethanol, propanol and butanol are discharged (5) together with water from the bottom of the column. The low-boilers which have a lower boiling point than THF, such as methanol, are withdrawn overhead via line (12) with THF, partially condensed by a heat exchanger and passed as reflux (13) back into column (1). The column (1) has, disposed above the inlet (4), a sidestream takeoff (6), through which a preferably liquid THF/water mixture (which may, however, be gaseous or a liquid/gas mixture) is withdrawn and introduced with increasing pressure via a pump into the side of the intermediate pressure column (2) through a feed for this stream disposed between half of the theoretical number of plates in the column and the head of the column.

The sidestream takeoff (6) is disposed between the 20th and 70th theoretical plate of the column (1), preferably between the 30th and 55th plate, more preferably between the 30th and 40th plate.

In the sidestream (6), THF is present in a weight ratio to water of from 13:1 to 25:1, preferably in a ratio of from 15:1 to 22:1.

The sidestream mixture (6) is fed into the upper section of the intermediate pressure column (2), between the 30th and 70th theoretical plate, preferably between the 40th and 60th plate, more preferably between the 50th and 60th plate. By shifting the azeotropic point of the THF/water mixture, the mixture is separated again in the intermediate pressure column (2). From the head of this intermediate pressure column, water-rich THF is condensed by a heat exchanger and recycled (7) into the first column between the sidestream takeoff (6) and the column bottom.

The bottom product of this intermediate pressure column (2) which is substantially water-free and consists of THF and high-boilers, for example, butyraldehyde, butyl methyl ether and further high-boiling O-functionalized CH compounds, is recycled via line (8) and may be mixed with crude water-containing THF, and reintroduced as feed into column (1) via line (4).

In the stripping section of the intermediate pressure column (2), THF accumulates to over 99% by weight. In order to avoid entraining the steam-volatile components into the column (3), a preferably liquid THF-rich stream, which may, however, also be gaseous or a liquid/gas mixture, is withdrawn between the vapor phase of the bottom and half of the number of theoretical plates in the column as a liquid sidestream (9) just above the base of the intermediate pressure column (2).

The sidestream (9) withdrawn from the column (2) comprises from 50 to 100% by weight of THF, preferably from 80 to 100% by weight, more preferably from 95 to 100% by weight of THF.

The sidestream (9) is fed into column (3) above the bottom. The feed point is between the 1st and 30th theoretical plate, preferably between the 1st and 15th plate, more preferably between the 5th and 10th plate. Pure THF is withdrawn at the top of the column (10) in liquid or gaseous form or as a liquid/gas mixture, preferably liquid, while the liquid bottom product is recycled into column (1) by a pump.

The examples which follow illustrate the invention.

EXAMPLES

Inventive Example 1

The distillation apparatus shown in the FIGURE was used. It consists of three columns (1), (2) and (3), of which column (1) has 48 and column (3) has 45 theoretical plates and both are operated at 1.3 bar absolute. Column (2), which is operated at elevated pressure of 8 bar, has 43 theoretical plates.

A water-containing THF mixture comprising 64.6% by weight of THF, 2.9% by weight of n-BuOH, 0.4% by weight of MeOH, 0.6% by weight of EtOH, 0.5% by weight of PrOH, 0.4% by weight of GBL, 124 ppm of BA and 115 ppm of BME was introduced into column (1) via the inlet (4). The remainder comprises further O-functionalized CH compounds and largely water.

Simultaneously, column (1) was fed with the bottom stream of column (2) via inlet (8) and with the bottom stream of column (3) via line (11). Column (1) was operated with a sidestream takeoff (6), a top takeoff (12) and a bottom takeoff (5). The reflux ratio based on the sidestream was 1.1. The bottom takeoff (5) drew off water and high-boilers.

The sidestream (6) withdrawn from column (1) was water-containing THF having a water content of 4% by weight and a THF concentration of 82.5% by weight. This corresponds to a THF:water ratio of 20.6.

The top takeoff (12) withdrew a little more than 0.05% of the feed. The top stream had a THF concentration of 64% by weight and a methanol content of 32% by weight.

The sidestream (6) of the first column was fed with increasing pressure into the second column (2) which was operated at 8 bar. The top stream (7) of the second column which contained virtually all the water and the bulk of the narrow-boiling components was recycled into the first column (1). A strongly THF-enriched stream is withdrawn as a liquid sidestream (9) just above the base and passed on into column (3).

The bottom stream of column (2) which was found to be virtually water-free was recycled via line (8). Ultrapure THF was withdrawn overhead (10) from the third column (3), while the bottom product was recycled into column (1) by a pump.

The concentrations of interfering secondary components in the pure THF are summarized in table 1.

Comparative Example

In comparison to the method described in DE-A 37 26 805, the sidestream takeoff (9) on the second column (2) according to the preceding inventive example 1 results in a distinct improvement in the depletion of secondary components in ultrapure THF. The separation results of these two methods are compared in table 1.

TABLE 1

|  | Butyraldehyde [% by weight] | Butyl methyl ether [% by weight] |
| --- | --- | --- |
| Water-containing THF mixture before distillation | 0.012 | 0.012 |
| Inventive example 1 | 0.001 | 0.001 |
| Comparative example | 0.005 | 0.003 |

We claim:

1. An improved process for distillatively purifying crude water-containing tetrahydrofuran by passing the crude tetrahydrofuran through three distillation columns, withdrawing water from the bottom of the first column, recycling water-containing tetrahydrofuran from the top of the second column into the first column, passing a sidestream of the first column into the second column, recycling the bottom product of the third column into the first column, and withdrawing an overhead stream at the top of the first column, wherein the improvement comprises passing a sidestream of the second column into the third column and recovering the purified tetrahydrofuran as the top product of the third column.

* * * * *